(12) United States Patent
Michalska et al.

(10) Patent No.: US 11,247,896 B2
(45) Date of Patent: Feb. 15, 2022

(54) LOCALIZED FUNCTIONALIZATION OF NANOTEXTURED SURFACES

(71) Applicant: UCHICAGO ARGONNE, LLC, Chicago, IL (US)

(72) Inventors: Martyna Michalska, Chicago, IL (US); Philip D. Laible, Downers Grove, IL (US); Ralu Divan, Darien, IL (US)

(73) Assignee: UChicago Argonne, LLC, Chicago, IL (US)

( * ) Notice: Subject to any disclaimer, the term of this patent is extended or adjusted under 35 U.S.C. 154(b) by 0 days.

(21) Appl. No.: 16/526,964

(22) Filed: Jul. 30, 2019

(65) Prior Publication Data

US 2020/0039819 A1 Feb. 6, 2020

Related U.S. Application Data

(60) Provisional application No. 62/712,786, filed on Jul. 31, 2018.

(51) Int. Cl.
| | |
|---|---|
| *B81C 1/00* | (2006.01) |
| *B81B 1/00* | (2006.01) |
| *A61M 37/00* | (2006.01) |
| *G03F 7/26* | (2006.01) |
| *G03F 7/38* | (2006.01) |

(52) U.S. Cl.
CPC ..... *B81C 1/00111* (2013.01); *A61M 37/0015* (2013.01); *B81B 1/008* (2013.01); *G03F 7/265* (2013.01); *G03F 7/38* (2013.01); *A61M 2037/0023* (2013.01); *A61M 2037/0053* (2013.01); *B81B 2201/055* (2013.01); *B81C 1/00388* (2013.01); *B81C 2201/0157* (2013.01)

(58) Field of Classification Search
None
See application file for complete search history.

(56) References Cited

U.S. PATENT DOCUMENTS

| | | | |
|---|---|---|---|
| 2003/0104296 A1 | 6/2003 | Hamano et al. | |
| 2011/0257040 A1* | 10/2011 | Turner | B01J 19/0046 |
| | | | 506/16 |
| 2012/0136312 A1 | 5/2012 | Terahara et al. | |
| 2012/0251611 A1 | 10/2012 | Luong-Van et al. | |
| 2012/0268823 A1 | 10/2012 | Morhard et al. | |
| 2016/0212989 A1 | 7/2016 | Juodkazis et al. | |
| 2018/0272045 A1 | 9/2018 | Gifford et al. | |

(Continued)

FOREIGN PATENT DOCUMENTS

WO   WO-2013/007354 A1   1/2013

OTHER PUBLICATIONS

Adams & Hunter, "Adaptation of intracytoplasmic membranes to altered light intensity in Rhodobacter sphaeroides," Biochimica et Biophysica Acta (BBA)—Bioenergetics 1817(9), pp. 1616-1627 (2012).

(Continued)

*Primary Examiner* — Jiong-Ping Lu
(74) *Attorney, Agent, or Firm* — Foley & Lardner LLP

(57) ABSTRACT

A material with a nanotexture comprising structures extending from a substrate. The structures are modified by coating the nanotexture with a protective coating and partially removing the coating, exposing a portion of the structure for functionalization.

20 Claims, 11 Drawing Sheets

(56) References Cited

U.S. PATENT DOCUMENTS

2019/0037841 A1 2/2019 Zhang et al.

OTHER PUBLICATIONS

Anselme, et al., "The interaction of cells and bacteria with surfaces structured at the nanometre scale," Acta Biomaterialia 6(10), pp. 3824-3846 (2010).

Atthi, et al., "Increasing Active Surface Area to Fabricate Ultra-Hydrophobic Surface by Using 'Black Silicon'with Bosch Etching Process," Journal of Nanoscience and Nanotechnology 12(6), pp. 4919-4927 (2012).

Bandara, et al., "Bactericidal Effects of Natural Nanotopography of Dragonfly Wing on *Escherichia coli*," ACS Applied Materials & Interfaces 9(8), p. 6746-6760 (2017).

Bhadra, et al., "Antibacterial titanium nano-patterned arrays inspired by dragonfly wings," Scientific Reports 5, 16817, 12 pages (2015).

Campoccia, et al., "A review of the biomaterials technologies for infection-resistant surfaces," Biomaterials 34(34), pp. 8533-8554 (2013).

Chen, et al., "Versatile antimicrobial peptide-based ZnO quantum dots for in vivo bacteria diagnosis and treatment with high specificity," Biomaterials 53, pp. 532-544 (2015).

Dickson, et al., "Nanopatterned polymer surfaces with bactericidal properties," Biointerphases 10(2), 021010, 8 pages (2015).

Diu, et al., "Cicada-inspired cell-instructive nanopatterned arrays," Scientific Reports 4, 7122, 7 pages (2014).

Dou, et al., "Bioinspired Hierarchical Surface Structures with Tunable Wettability for Regulating Bacteria Adhesion," ACS Nano 9(11), pp. 10664-10672 (2015).

Drelich & Chibowski, "Superhydrophilic and Superwetting Surfaces: Definition and Mechanisms of Control," Langmuir 26(24), pp. 18621-18623 (2010).

Drelich, et al., "Hydrophilic and superhydrophilic surfaces and materials," Soft Matter 7, pp. 9804-9828 (2011).

Duran, et al., "Antimicrobial activity of biogenic silver nanoparticles, and silver chloride nanoparticles: an overview and comments," Applied Microbiology and Biotechnology 100(15), pp. 6555-6570 (2016).

Dylla, et al., "Species differences in unlocking B-side electron transfer in bacterial reaction centers," FEBS Letters 590(16), pp. 2515-2526 (2016).

Elbourne, et al., "Nano-structured antimicrobial surfaces: From nature to synthetic analogues," Journal of Colloid and Interface Science 508, pp. 603-616 (2017).

Fisher, et al., "Bactericidal activity of biomimetic diamond nanocone surfaces," Biointerphases 11, 011014, 6 pages (2016).

Friedlander, et al., "Bacterial flagella explore microscale hummocks and hollows to increase adhesion," Proceedings of the National Academy of Sciences USA 110(14), pp. 5624-5629 (2013).

Gao, et al., "Application of Black Silicon for Nanostructure-Initiator Mass Spectrometry," Analytical Chemistry 88(3), pp. 1625-1630 (2016).

Genkin, et al., "Topological Defects in a Living Nematic Ensnare Swimming Bacteria," Physical Review X 7, 011029, 14 pages (2017).

Green, et al., "High Quality Bioreplication of Intricate Nanostructures from a Fragile Gecko Skin Surface with Bactericidal Properties," Scientific Reports 7, 41023, 12 pages (2017).

Gudur & Ji, "Bio-Applications of Nanopillars," Frontiers in Nanoscience and Nanotechnology 2(6), pp. 1-10 (2016).

Guttenplan, et al., "The cell biology of peritrichous flagella in Bacillus subtilis," Molecular Microbiology 87(1), pp. 211-229 (2013).

Hasan, et al., "Nanoscale Topography on Black Titanium Imparts Multi-biofunctional Properties for Orthopedic Applications," Scientific Reports 7, 41118, 13 pages (2017).

Hasan, et al., "Selective bactericidal activity of nanopatterned superhydrophobic cicada Psaltoda claripennis wing surfaces," Applied Microbiology and Biotechnology 97(20), pp. 9257-9262 (2013).

Henriques, et al., "Control of cell shape and elongation by the rodA gene in Bacillus subtilis," Molecular Microbiology 28(2), pp. 235-247 (1998).

Ito, et al., "Materials tor enhancing cell adhesion by immobilization of cell-adhesive peptide," Journal of Biomedical Materials Research 25(11), pp. 1325-1337 (1991).

Ivanova, et al., "Bactericidal activity of black silicon," Nature Communications 4, 2838, 7 pages (2013).

Ivanova, et al., "Natural Bactericidal Surfaces: Mechanical Rupture of Pseudomonas aeruginosa Cells by Cicada Wings," Small 8(16), pp. 2489-2494 (2012).

Jansen, et al., "Black silicon method X: a review on high speed and selective plasma etching of silicon with profile control: an in-depth comparison between Bosch and cryostat DRIE processes as a roadmap to next generation equipment," Journal of Micromechanics and Microengineering 19(3), 41 pages (2009).

Jansen, et al., "The black silicon method: a universal method for determining the parameter setting of a fluorine-based reactive ion etcher in deep silicon trench etching with profile control," Journal of Micromechanics and Microengineering 5(2), pp. 115-120 (1995).

Ji, et al., "Antibacterial applications of graphene-based nanomaterials: Recent achievements and challenges," Advanced Drug Delivery Reviews 105(B), pp. 176-189 (2016).

Kelleher, et al., "Cicada Wing Surface Topography: An Investigation into the Bactericidal Properties of Nanostructural Features," ACS Applied Materials & Interfaces 8(24), pp. 14966-14974 (2016).

Koebnik, et al., "Structure and function of bacterial outer membrane proteins: barrels in a nutshell," Molecular Microbiology 37(2), pp. 239-253 (2000).

Lee, et al., "Biocompatible Multifunctional Black-Silicon for Implantable Intraocular Sensor," Advanced Healthcare Materials 6(4), 1601356, 12 pages (2017).

Linklater, et al., "Comment on 'Bactericidal Effects of Natural Nanotopography of Dragonfly Wing on *Escherichia coli*'," ACS Applied Materials & Interfaces 9(35), pp. 29387-29393 (2017).

Liu, et al., "Black silicon: fabrication methods, properties and solar energy applications," Energy & Environmental Science 7, pp. 3223-3263 (2014).

Liu, et al., "Sharper and Faster "Nano Darts" Kill More Bacteria: A Study of Antibacterial Activity of Individually Dispersed Pristine Single-Walled Carbon Nanotube," ACS Nano 3(12), pp. 3891-3902 (2009).

Lu & Barron, "In-Situ Fabrication of a Self-Aligned Selective Emitter Silicon Solar Cell Using the Gold Top Contacts to Facilitate the Synthesis of a Nanostructured Black Silicon Antireflective Layer Instead of an External Metal Nanoparticle Catalyst," ACS Applied Materials & Interfaces 7(22), pp. 11802-11814 (2015).

Martines, et al., "Superhydrophobicity and Superhydrophilicity of Regular Nanopatterns," Nano Letters 5(10), pp. 2097-2103 (2005).

Min, et al., "Designer Dual Therapy Nanolayered Implant Coatings Eradicate Biofilms and Accelerate Bone Tissue Repair," ACS Nano 10(4), pp. 4441-4450 (2016).

Nguyen, et al., "Natural Insect and Plant Micro-/Nanostructsured Surfaces: An Excellent Selection of Valuable Templates with Superhydrophobic and Self-Cleaning Properties," Molecules 19(9), pp. 13614-13630 (2014).

Nie, et al., "Mussel-Inspired Antibacterial and Biocompatible Silver-Carbon Nanotube Composites: Green and Universal Nanointerfacial Functionalization," Langmuir 32(23), pp. 5955-5965 (2016).

Nowlin, et al., "Adhesion-dependent rupturing of *Saccharomyces cerevisiae* on biological antimicrobial nanostructured surfaces," Journal of the Royal Society Interface 12(102), 12 pages (2014).

Oestreicher, et al., "A comparison of the surface nanostructure from two different types of gram-negative cells: *Escherichia coli* and Rhodobacter sphaeroides," Micron 72, pp. 8-14 (2015).

Ostrikov, et al., "Bactericidal effects of plasma-modified surface chemistry of silicon nanograss," Journal of Physics D: Applied Physics 49(30), 9 pages (2016).

Pezoldt, et al., "Black luminescent silicon," Physica Status Solidi 8(3), pp. 1021-1026 (2011).

(56) References Cited

OTHER PUBLICATIONS

Pham, et al., "Nanotopography as a trigger for the microscale, autogenous and passive lysis of erythrocytes," Journal of Materials Chemistry B 2, pp. 2819-2826 (2014).
Pham, et al., "'Race for the Surface': Eukaryotic Cells Can Win," ACS Applied Materials & Interfaces 8(34), pp. 22025-22031 (2016).
Pogodin, et al., "Biophysical Model of Bacterial Cell Interactions with Nanopatterned Cicada Wing Surfaces," Biophysical Journal 104(4), pp. 835-840 (2013).
Raj, et al., "*Rhodobacter viridis* sp. nov., a phototrophic bacterium isolated from mud of a stream," International Journal of Systematic and Evolutionary Microbiology 63, pp. 181-186 (2013).
Rhodes, "The Characterization of Pseudomonas fluorescens," The Journal of General Microbiology 21(1), pp. 221-268 (1959).
Sainiemi, et al., "Non-Reflecting Silicon and Polymer Surfaces by Plasma Etching and Replication," Advanced Materials 23(1), pp. 122-126 (2011).
Schmidt, et al., "Towards easily reproducible nano-structured SERS substrates," 2009 IEEE Sensors, pp. 1763-1767 (2009).
Schneider, et al., "NIH Image to ImageJ: 25 years of image analysis," Nature Methods 9, pp. 671-675 (2012).
Schneider, et al., "The Influence of Structure Heights and Opening Angles of Micro- and Nanocones on the Macroscopic Surface Wetting Properties," Scientific Reports 6, 21400, 9 pages (2016).
Sengstock, et al., "Structure-related antibacterial activity of a titanium nanostructured surface fabricated by glancing angle sputter deposition," Nanotechnology 25(19), 195101, 11 pages (2014).
Singh, "Biotechnological applications of supersonic cluster beam-deposited nanostructured thin films: Bottom-up engineering to optimize cell-protein-surface interactions," Journal of Biomedical Materials Research 101(10), pp. 2994-3008 (2013).
Singh, et al., "Hydrophobic pinning with copper nanowhiskers leads to bactericidal properties," PLoS ONE 12(4), e0175428, 14 pages (2017).
Sjostrom, et al., "Bactericidal nanospike surfaces via thermal oxidation or Ti alloy substrates," Materials Letters 167, pp. 22-26 (2016).
Sportelli, et al., "Recent advances in the synthesis and characterization of nano-antimicrobials," TrAC Trends in Analytical Chemistry 84(A), pp. 131-138 (2016).
Steglich, et al., "The structural and optical properties of black silicon by inductively coupled plasma reactive ion etching," Journal of Applied Physics 116, 173503, 13 pages (2014).
Susarrey-Arce, et al., "Bacterial viability on chemically modified silicon nanowire arrays," Journal of Materials Chemistry B 4, pp. 3104-3112 (2016).
Taguchi, et al., "Biochemical characterization and electron-transfer reactions of sym1, a Rhodobacter capsulatus reaction center symmetry mutant which affects the initial electron donor," Biochemistry 31(42), pp. 10345-10355 (1992).
Taute, et al., "High-throughput 3D tracking of bacteria on a standard phase contrast microscope," Nature Communications 6, 8776, 9 pages (2015).
Tripathy, et al., "Natural and bioinspired nanostructured bactericidal surfaces," Advances in Colloid and Interface Science 248, pp. 85-104 (2017).

Truong, et al., "The susceptibility of *Staphylococcus aureus* CIP 65.8 and Pseudomonas aeruginosa ATCC 9721 cells to the bactericidal action of nanostructured Calopteryx haemorrhoidalis damselfly wing surfaces," Applied Microbiology and Biotechnology 101(11), pp. 4683-4690 (2017).
Turner, et al., "Different walls for rods and balls: the diversity of peptidoglycan," Molecular Microbiology 91(5), pp. 862-874 (2014).
Tuson, et al., "Measuring the stiffness of bacterial cells from growth rates in hydrogels of tunable elasticity," Molecular Microbiology 84(5), pp. 874-891 (2012).
Vadillo-Rodriguez & Dutcher, "Dynamic viscoelastic behavior of individual Gram-negative bacterial cells," Soft Matter 5, pp. 5012-5019 (2009).
Vadillo-Rodriguez & Dutcher, "Viscoelasticity of the bacterial cell envelope," Soft Matter 7, pp. 4101-4110 (2011).
Wu, et al., "Nanostructured surface topographies have an effect on bactericidal activity," Journal of Nanobiotechnology 16, 20, 9 pages (2018).
Xie, et al., "Mechanical Model of Vertical Nanowire Cell Penetration," Nano Letters 13(12), pp. 6002-6008 (2013).
Xue, et al., "Theoretical study on the bactericidal nature of nanopatterned surfaces," Journal of Theoretical Biology 385, pp. 1-7 (2015).
Zhang, et al., "Superhydrophobic surfaces for the reduction of bacterial adhesion," RSC Advances 3, pp. 12003-12020 (2013).
Chu, et al., "Localized Three-Dimensional Functionalization of Bionanoreceptors on High-Density Micropillar Arrays via Electrowetting," Langmuir 34(4), pp. 1725-1732 (2018).
Lee, et al., "Protein patterning on silicon-based surface using background hydrophobic thin film," Biosensors and Bioelectronics 18(4), pp. 437-444 (2003).
Liu, et al., "Black silicon: fabrication methods, properties and solar energy applications," Energy & Environmental Science 7(10), pp. 3223-3263 (2014).
Park, et al., "Selective Surface Functionalization of Silicon Nanowires via Nanoscale Joule Heating," Nano Letters 7(10), pp. 3106-3111 (2007).
Yun, et al., "A self-heated silicon nanowire array: selective surface modification with catalytic nanoparticles by nanoscale Joule heating and its gas sensing applications," Nanoscale 5, pp. 6851-6856 (2013).
Cheng, et al., "Fabrication of periodic arrays of needle-like Si nanowires on (001)Si and their enhanced field emission characteristics," RSC Advances 7(39), pp. 23935-23941 (2017).
Choi & Kim, "Fabrication of a dense array of tall nanostructures over a large sample area with sidewall profile and tip sharpness control," Nanotechnology 17(21), pp. 5326-5333 (2006).
Dorrer & Ruhe, "Wetting of Silicon Nanograss: From Superhydrophilic to Superhydrophobic Surfaces," Advanced Materials 20(1), pp. 159-163 (2008).
Hu, et al., "Bio-inspired silicon nanospikes fabricated by metal-assisted chemical etching for antibacterial surfaces," Applied Physics Letters 111(25), 253701, 5 pages (2017).
Susarrey-Arce, et al., "Bacterial viability on chemically modified silicon nanowire arrays," Journal of Materials Chemistry B 4(18), pp. 3104-3112 (2016).

\* cited by examiner

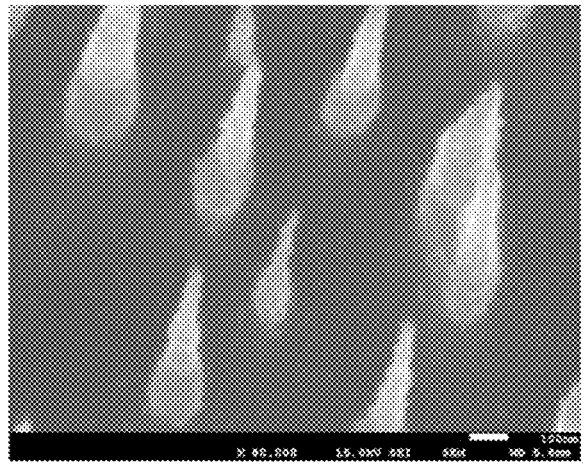 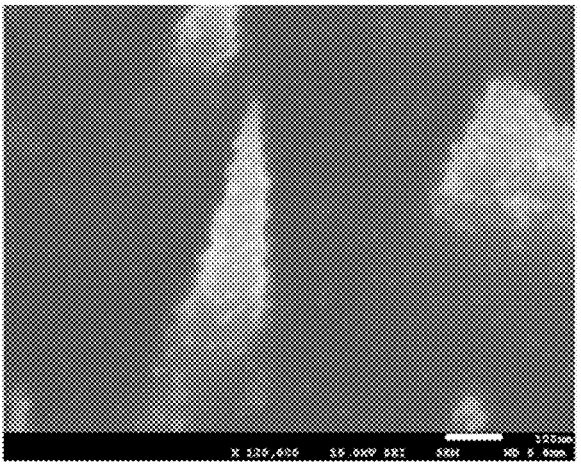
FIG. 13A  FIG. 13B
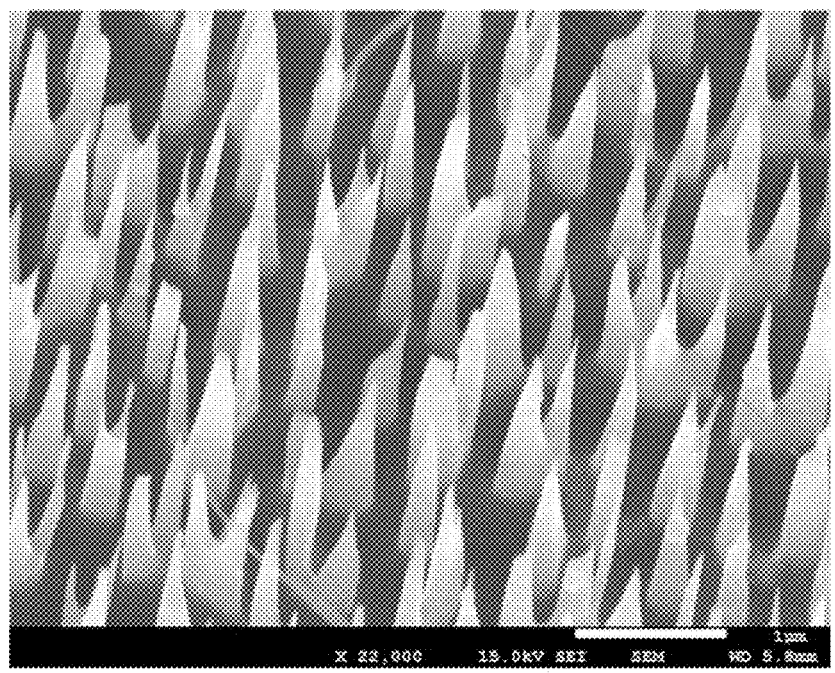
FIG. 14

LOCALIZED FUNCTIONALIZATION OF NANOTEXTURED SURFACES

CROSS-REFERENCE TO RELATED APPLICATIONS

This application claims priority to and the benefit of U.S. Provisional Patent Application No. 62/712,786, filed on Jul. 31, 2018, the content of which is incorporated by reference herein in its entirety.

STATEMENT OF GOVERNMENT INTEREST

This invention was made with government support under Contract No. DE-AC02-06CH11357 awarded by the United States Department of Energy to UChicago Argonne, LLC, operator of Argonne National Laboratory. The government has certain rights in the invention.

TECHNICAL FIELD

The present disclosure relates generally to micromanufacturing and nanomanufacturing, more specifically to functionalization of nanotextured surfaces.

BACKGROUND

Textured surfaces provide materials critical to the function of a wide range of devices. In particular, nanotextured materials provide a wide range of useful properties that can be harnessed to create useful apparatus. However, nanotextured surfaces also present problems. The size and physical arrangement of individual structures on a nanotextured surface make modifying such structures difficult. Thus, functionalizing nanotextured structures remains a challenge.

Recently, high-density micropillar arrays were selectively biofunctionalized using the electrowetting technique. The patterning was effective but this technology is suitable for only hydrophobic structures. The concept of using protective layer was utilized by Park, et al. ("*Selective Surface Functionalization of Silicon Nanowires via Nanoscale Joule Heating*," Nano Letters 7(10), pp. 3106-3111 (2007)), who employed localized heating effect to selectively ablate a protective, chemically-inert polymer layer from a region of the chosen silicon nano-wire. Although the method can be very selective and therefore, of interest of micro-mechanical systems ("MEMS") and nano-mechanical systems ("NEMS") communities requiring high precision, such a method has several failings, including not being as scalable as the methods described herein.

Generally, modification of surfaces having micro and nano features has used either global surface modification techniques or local surface modification techniques. Global techniques, such as self-assembled monolayer coatings or vapor deposition, apply a coating to the entire nanotextured material. Local surface modification relies upon a physically isolated contact or interaction with a portion of the nanotextured material to create a localized modification. However, the ability to selectively functionalize portions of a nanotextured structure while allowing for scalability and throughput remains a complex problem for existing technologies, as does providing a robust nanostructure system with sufficient strength for some applications.

SUMMARY

One embodiments relates to a method for functionalizing a nanotextured material comprising: forming a nanotextured material having a plurality of structures extending in a first dimension and each of the plurality of structures having a distal portion; applying a protective coating to the nanotextured material; removing a portion of the protective coating and exposing at least some of the distal portions of the plurality of structures; modifying the exposed distal portions with a first functional group; and removing the protective coating.

Another embodiment relates to a nanotextured material. A substrate has a plurality of structures extending therefrom forming a nanotexture. Each of the plurality of structures is attached to the substrate at a proximate end, having a distal portion extending from the substrate. At least one of the distal portions has a functional group associated therewith.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore not to be considered limiting of its scope, the disclosure will be described with additional specificity and detail through use of the accompanying drawings.

FIG. 9A shows unetched black silicon ("bSi") wafer spin-coated with photoresist that is and FIG. 9B shows bSi wafer spin-coated with photoresist that is following 2 min etching with oxygen plasma. FIG. 9C shows unetched and FIG. 9D shows following 2 min etching with oxygen plasma.

FIG. 10A shows the temporal evolution/disappearance of the thickness of that layer upon mild etching with oxygen plasma seen in FIGS. 10B and 10C. The rate is ca. 0.2 μm/min.

FIGS. 11A-1D illustrate transmission electron micrographs of: citrate-stabilized Au nanoparticles of sizes 3-15 nm (left) and Au nanopillars locally immobilized on nanopillars (only appearing on the upper half).

FIGS. 13A-13B show Au nanoparticles attached to tips of nanoprotrusions with the photo resist layer still intact.

FIG. 14 shows Au nanoparticles attached to tips of nanoprotrusions from positive control with the photo-resist ("PR") layer removed.

Figure 1:
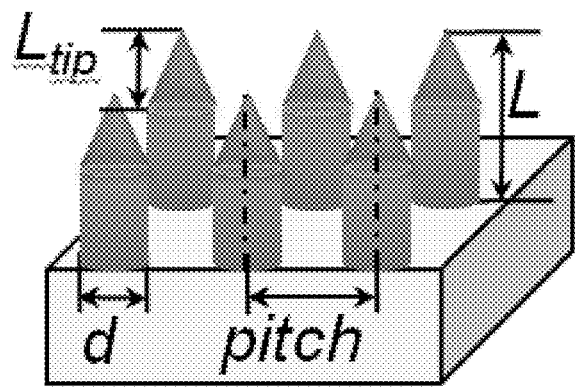
FIG. 1 is an illustration of one embodiment of one embodiment of nanotextured material wherein the nanostructures are pillars.
Figure 2A:
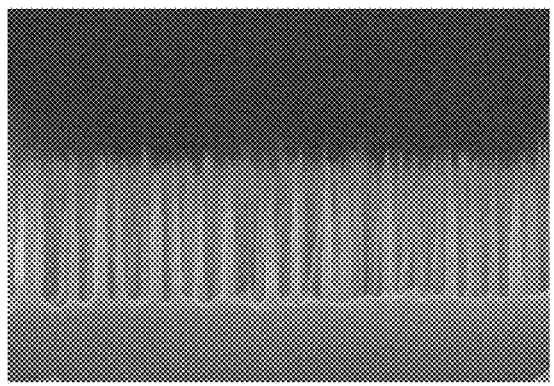
FIG. 2A shows an illustration of sample of a nanotextured material having nano structures on a substrate.
Figure 2B:
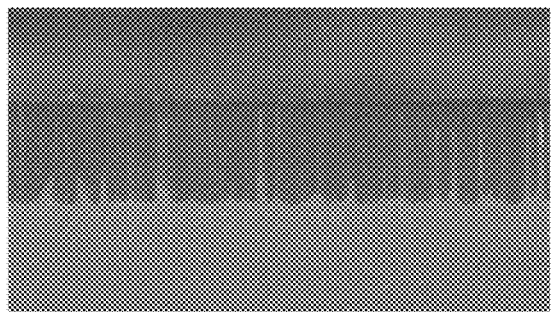
FIG. 2B shows the sample of FIG. 2A having been fully embedded in a protective coating.
Figure 2C:
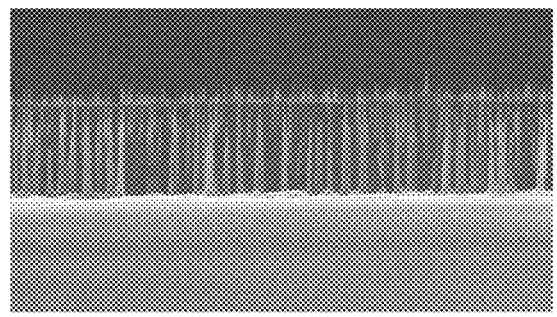
FIG. 2C shows the sample FIG. 2B after removal of a portion of the coating to expose a portion of the structures.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Nanotextured materials existing in several forms. Generally, nanotextured materials are those materials that have a surface with at least one dimension in the nanoscale (i.e., materials that are rough, nanopatterned, non-smooth, etc.). That is, the materials have a surface with a plurality of nanostructures extending therefrom having a height from the underlying surface (i.e., an amplitude roughness, of 0.1 nm to 999 nm, such as 0.1 nm to 100 nm). Nanostructures can exhibit heterogeneity or homogeneity, and only one dimension may have structures. Nanotextured materials may exhibit a profile roughness with surface elements that repeat regularly or non-regularly at intervals not exceeding 10 μm.

In one embodiment, the nanostructures have a general shape of a cone, pillar, fiber nano-wire, truncated cones, reentrant structures, nano-hoodoos, nanoholes, spires, or the like. The reentrant structures can be used for superhydrophobicity and superoleophobicity, self-cleaning surfaces, slip surfaces, etc. The nanostructures may have a range of aspect ratios (0.1 to 25) with tip angles in the range of 1° to 175°. It should be appreciated that a nanotextured material may comprise nanostructures of different shapes and or sizes. FIG. 1 illustrates one embodiment where the nanostructures are a pillar with a conical tip. In the FIG. 1 representation of the pillars, where L is total length, $L_{tip}$ is a length of sharpened tip, d is base diameter, and pitch is a distance between centers of two pillars (spacing+diameter). Further, functionalizing the structures can impact the performance of the nanotextured materials in a variety of applications. For example, the sharpness/bluntness will impact the utility of the tip functionalized variants. In yet another example, the tip of the structures can be functionalized to have attractive or repulsive properties relative to a desired object or material.

The nanotextured material comprises one or more materials, for example silicon. The silicon may be, in one example, a nanotextured material comprising "black silicon" can be utilized. The silicon may have a $SiO_2$ passivation layer that may be modified. Further, glass substrates may be used, such as fused silica, quartz, thermally grown $SiO_2$ or PECVD (plasma enhanced chemical vaporization deposition) with grown $SiO_2$ on top of various substrates. The nanostructure material comprises material that is capable of having high-aspect-ratio protrusions. These protrusions may comprise a separate material such as $SiN_3$, ZnO nanowires, nanotextured polymers (PMMA etc.).

Black silicon fabrication may be carried out as known in the art, including by use of the inductively coupled plasma reactive ion etching ("ICP-RIE") technique. Using the ICP-RIE process, bSi is fabricated as a non-masking process in $O_2$ and $SF_6$ atmosphere, whereas a continuous competition between the etching fluorine radicals and the side-wall-passivating oxygen radicals occurs, such as is described in "*Black silicon: fabrication methods, properties and solar energy applications*" (Liu, et al., Energy Environ. Sci. 7(10), pp. 3223-3263 (2014)), incorporated herein by reference. In a further embodiment, the etched surfaces can be migrated over post-synthesis to another surfaces as the substrate to support the bSi material or can use nanoimprinting techniques to transfer the nanopillars to other types of materials that conform to unique surface structures. Further, the nanopillar surfaces can be coated with atomic layers (including partial layers, such as islands) of other metals or metal oxides. They can be readily surface-modified for any exposed functionalization using silane chemistry. In addition, during the synthesis, wafers with different amounts of impurities/dopants can be used. For example, in some embodiments described further below, the nanopillar materials include boron.

In one embodiment, a method for selective surface modification and/or functionalization of nanotextured surfaces comprises: 1) deposition of a protective layer, 2) removal of at least a portion of the protective layer to expose at least a portion of the structures of the nanotextured surface, 3) modification of the exposed portion of the structures, 4) removal of the remaining protective layer, and 5) optionally, further modification of the modified structures. In general, a resist layer is selected so that it penetrates to the base of the nanostructures. The resist layer should be amenable to etching but also fairly resistant. The resist layer should resist being eaten away by surface modification chemistries, and final removal of the resist and/or the modifying chemistry entities should not alter the nanostructure further.

In a first step, an existing nanotextured material is coated with a protective layer. The protective layer may be deposited, such as by physical deposition (e.g., spin coating dipping methods, etc.), as well as chemical vapor deposition, such as by ALD. ALD is useful as it creates conformal layers along a nanostructure that could be further etched out only from the top of the nanostructure, leaving behind a lateral wall along the nanostructure length (height) so that only top (such as the tip) can be modified.

In one embodiment, prior to depositing the coating, the nanotextured surface has all water removed, or is otherwise made less hydrophilic. For example, in one embodiment, the nanotextured surface is washed or cleaned with an organic solvent (e.g., acetone, toluene). For example, the surface of bSi is superhydrophilic (as many surfaces are after plasma activation—typical surface cleaning during fabrication to remove organic contaminants and allow for better resist/ primer etc. coverage), so it readily adsorbs water on the surface, which affects the coating. In some examples noted below, the surfaces were cleaned with acetone and spin-coated with photoresist immediately thereafter. Alternatively (if not spin coated immediately), nanotextured materials can be placed on the hot plate or other heating environment (such as at 150° C. to evaporate water and cool down) and spin coated after.

The protective coating should fill the spaces between the structures. For embodiments using a spin coating process, the process may proceed through a one-step process or a multi-step process. The parameters for spin coating should be selected to achieve a desired coating thickness based on the desired functionalization on the nanostructures. For example, the parameters include (i) spin speed (rpm), (ii) acceleration (especially important for higher surface areas at higher speeds), and (iii) dwell time. Overall, these parameters are given by manufacturers to achieve given thickness on the smooth substrate with a given device. In view of these device parameters and the pattern/roughness of the nano-textured surface, the overall parameters should be balanced to provide the desired thickness and coverage.

With regard to the use of a 1-step or 2-step process, as described, the results were reviewed for the surfaces with 4 pillars/$\mu m^2$ and after covering the surfaces with the resist via 1-step or 2-step method. The analysis used gentle beam images where visible bumps were counted (bumps=slightly taller pillars than majority, likely covered with a thin resist). The results were 0.7 vs. 1 pillars/$\mu m^2$ for 1-step and 2-step, respectively, which indicates better coverage for 1-step protocol. In certain examples below, a one-step process with a 3000 RPM (1500 acceleration) for 35s was applied. It should be appreciated that for particularly dense feature arrangements on the nanotextured surface, the resist may need to be diluted prior to application.

Figure 3:
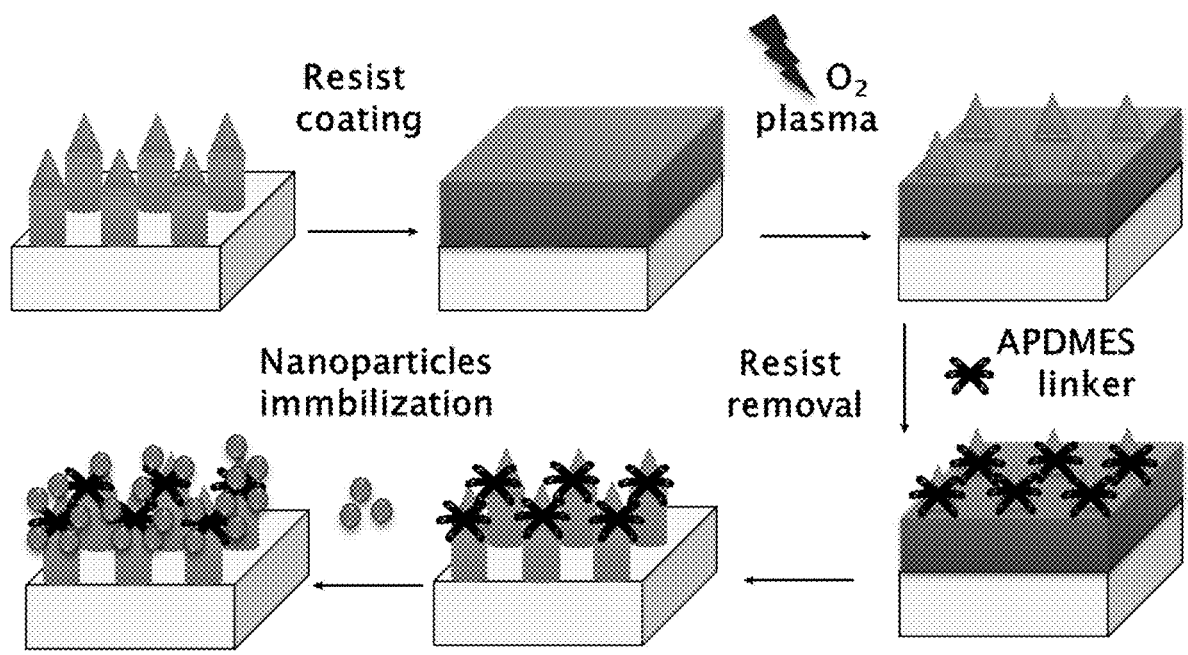
FIG. 3 is a schematic showing one method of fabricating functionalized nanotextured material.

The protective layer is selected to comprise a material that is resistive to the modification described below in step 3. For example, the protective layer may be a photo-resist, such as, but not limited to, polymers (e.g., those manufactured by Shipley with brands like Novaloc® and S1805, S1811, S1813, S1818, S1827 from the Shipley MICROPOSIT' series). The viscosity of the resists must accommodate the spacing and height of the structures. The resists can be diluted if needed and additive coating steps employed. Alternatively, nanostructures can be coated not entirely, then treated with brief etch, such as plasma, to remove residual layer of the sidewalls of the upper parts that are targeted for modification. The resist should be chemically inert towards further chemical modifications and should be possible to remove without changing the structure of the nanotextured materials. That is, the protective layer should prevent physical and chemical modification of the covered nanotextured materials structure. In one embodiment, the protective layer is uniform. In one embodiment, the protective layer is deposited conformally (following the contour of the rough surface). FIG. 3 illustrates a schematic depiction of a protective coating deposited on a set of nanopillars.

In a second step, a first portion of the protective layer is removed, leaving a partially coated nanotextured material, with the nanostructures having an exposed portion extending above the remaining resist. The protective layer may be removed by reaction ion etching (e.g., oxygen plasma etching) or chemical treatment (e.g., by solvents or caustic agents). The etching not only exposes the regions to be modified by removing some of the resist, but also hydroxylates the surface (as indicated by the water contact angle). Note, etching with oxygen plasma does not affect the structure of the tips of the nanostructures as it works selectively on organic composition of resist and ashes it. However, the oxygen plasma exposure does modify the surface energy of the tips by breaking Si—O bonds, inducing dangling bonds, and —OH groups, for instance. In one embodiment, etching can be employed to sharpen the exposed tips of the nanostructure when selective gases are employed. For example, $SF_6$ could isotopically etch the tips. This is most likely done prior to the segmented chemical modification process, but it can be done during or after. In one embodiment, the first portion is a uniform depth of the protective layer such that a distal (relative to the surface) portion of the structure is uncovered by the removal. FIG. 3 illustrates the application of an oxygen plasma etch to remove a portion of the protective layer, uncovering the tips of the pillars. It should be appreciated that further masking techniques could be used to selectively etch only certain portions of the protective coating. Double masking could be utilized for complex modifications involving exposures of different portions of the structures at different times in the process.

In one embodiment, a modification of the nanostructure may include the application of a second masking or resist material, such as by click chemistry or other linking chemistry, to the tip of the nanostructure. The second resist would allow an etch that removes the first resist and material of the nanotextured materials not covered by the second resist (which, itself, may then be removed). These embodiments would allow for structures where the nanostructure has been undercut, such as forming arrow or hoodoo shapes.

In one embodiment, the partially coated nanotextured materials may be cut into segments for individual functionalization. For example, a diamond knife or dicing saw may be used to segment the materials.

In a third step, the exposed portion of the structures is subjected to a modification. For example, the exposed portion may be chemically modified (e.g., with simple silane chemistry and the wealth of silane monomers that are available commercially). In one embodiment, the attachment of surface treatments would be covalent. In a further embodiment, the functionalization may be by ionic interactions and hydrophobic interactions and combinations of these and other surface adherence strategies. For example, in FIG. 3 the pillar tips are illustrated as being modified with a 3-Aminopropyl-methyl-diethoxysilane ("APDMES") linker. As a further example, additional samples were modified using mercaptopropylmethyldimethoxy silane ("MPMDMS"). In one embodiment, particularly for more closely packed nanostructures, the modification may comprise a linking modifier, such long chain polymers, that link one nanostructure to another. Further, other silanes could be used that provide co-localized surface modification where, for example, silane possesses thiol and amine or carboxy group spaced from each other, and later two different molecules are attached using various chemistries and will result and proximity. More generally, one can select the chemistry for modification to force spatial arrangement.

The photoresist must be considered when selecting a solvent for the modification solution. For example, the tested photoresist was soluble/removed by the following solvents: methanol, ethanol, isopropyl alcohol, chloroform, and acetone. The chemistry of the modifying materials, such as silanes should also be considered. For example, silanes that contain methoxy and ethoxy groups, upon hydrolysis of those groups, methanol and ethanol are released that locally dissolve photoresist, thus exposing more surface of the pillars. Silanization occurs quickly, 1-2 h is enough for a successful modification where the concentration is below 1% v/v (in toluene or water), up to 50 ul per 1 $cm^2$ is used, the photoresist removal is negligible. It should be considered that these newly released areas were not exposed to oxygen plasma before and, thus, hydroxylated so they won't be modified (the newly exposed surface will likely always some have some hydroxyls on the surface). Toluene was the preferred of solvent for washing: well miscible with silane; aprotic; and rapid silane polymerization prevented. Water or aqueous materials as a solvent are not idea as water is immiscible with silanes; emulsions created may cause inhomogeneous surface modification (although not observed thus far); and can cause rapid polymerization (silane degradation).

Further, some embodiments use ethoxy-free silanes, such as chloro-silanes or cyclic azasilanes, which will not release products that further react with the resist. For example, chlorosilanes will release HCL rather than an alcohol (as is the case for ethoxy silanes. Further, branched (or bis) silanes, such as dipodal silanes, may also be used. The same spin-coated S1818 resist on the Si wafers described with regard to the examples below show no degradation of photoresist layer when exposed to HCL. For example:
  1. added 200 ul of 3.7% HCl and incubated for 15 min and observed no effect of the photoresist (if it dissolves, it would have turned an intense yellow)
  2. added 200 ul of 100% Trichlorododecylsilane and incubated for 10 min. No effect has been observed. Washed the surface and added acetone—immediately the surface has been cleaned and the wastes were yellow, indicating the resist was still there
  3. that is not the case with pure methoxy- or ethoxy-based silanes. Using pure APTMES, for example, resist removal was observed within seconds. For this reason, certain embodiments use the diluted silanes as noted in conjunction with a solvent systems (e.g., toluene/water).

For the oxygen RIE, the key parameters are RF power and oxygen flow. To slow down the etching rate that would allow for better control in accuracy of the height of exposed parts, RF has to be lower (the range is range 30-200 W). If tall structures need a significant reduction in the resist layer, it is advisable to etch at lower RF to avoid resist heating up and therefore deforming, potentially peeling off the structures In one embodiment, the process selected to modify the exposed nanostructures utilizes components nonreactive with the resist. For example, water or toluene are preferred for certain resist that are reactive with otherwise common solvents, such as alcohols, methylene chloride, and acetone.

In one embodiment, a silanization process was utilized. Silane is reactive with many resists. The silane compound used for the silanization process may be diluted in a nonreactive (with both the silane compound and the resist) silanization solvent, such as water or toluene. Silanization solvent is preferably aprotic and miscible with silane, while preventing or retarding silane polymerization. The silane solution may have a concentration of range of 0.001 to 1%, such as 1% v/v silane compound/solvent. Note, it should be appreciated that the silane content may be selected to achieve full surface coverage of exposed portions or to only provide partial coverage, which may be in combination with another modification mechanism binding with the exposed surface.

In a fourth step, the remainder of the protective layer is removed. In one embodiment, additional masking may be utilized to provide for further selective modification of the structures.

In a fifth step, the modified structures may be further modified. For example, additional compounds may be bonded to the modified portion of the structures. As one example, one or more molecules may be conjugated to molecules bound to the structures through the modification step 3. For example, the unmodified structures or unmodified portions of individual structures be modified post-resist in a way that does not modify the portions already modified in step 3. As one specific non-limiting example, a layer of amines binding Protein A could be deposited on the exposed portion of the structures and could be followed by carboxyls attracting DNA Fragment A. Then a thiol can be attached that immobilizes Metabolite A.

In one embodiment, a polymeric network (permeable) is positioned at the top of the structures. Such a construct would enable the inclusion of chemicals, such as pharmaceutics, that could be slowly released through the porous network of the polymer or through the permeability of the network. Thus, such an embodiment could hide drugs underneath and have them slowly leak through the polymeric network or have triggered release with programmed destruction of the network. It should be appreciated that the reverse can also be constructed with a permeable network that allows select agents to be attracted and trapped below it within the bases of the structures. The polymeric network would initiate from the modified segments of the nanostructures and extend over to other modified segments of adjacent nanostructures. Effectively, this would provide a selective net or barrier to trap interesting chemical/protein/nucleotide/synthetic/organic moieties below and then allow for slow release out and through the netting. Some dense arrangements of nanostructures are long enough to be bridged by long silane monomers. Polymers and networks can be facilitated by multi-functional, branched (e.g., bis, tris, etc.) and/or long-extended silanes.

This method is facile, economical, uses standard fabrication techniques, and can be applied on the wafer-scale (usually 4-10 inches diameter and beyond), if needed. The area of modification can be readily tuned by varying the time of oxygen-plasma treatment. This step immediately introduces hydroxyl groups available for silane chemistry, for instance. Importantly, it does not affect the topography of nanopillars. The arrays of various densities can be processed by the simple changing of the viscosity of the protective polymer (photoresist). An additional advantage of the process that utilizes protectant is the ability to preserve fragile texturing. Such an approach also reduces costs as chemical reactants do not cover the entire surface area (typically very high for nano-rough surfaces) but only the targeted/exposed regions of pillar structures.

Figure 4A:
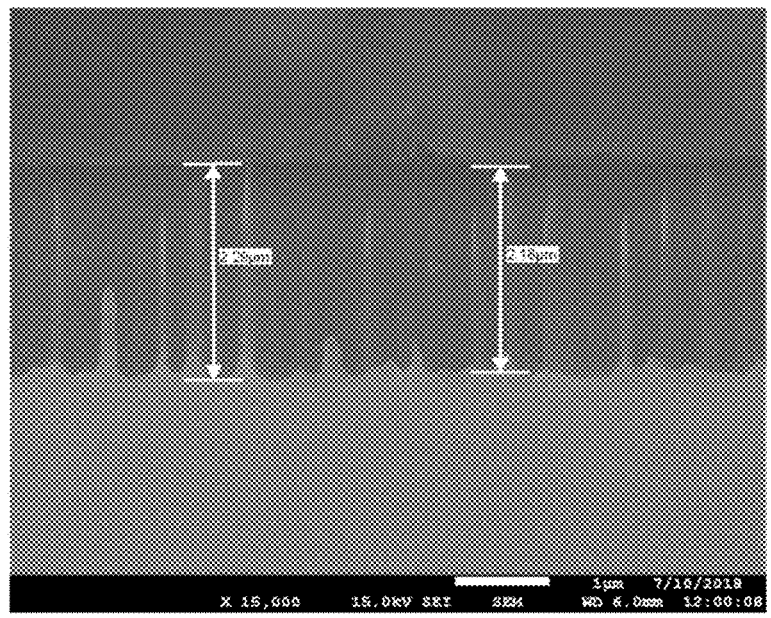
FIGS. 4A-4B show a cross-section of a nanotextured material with a protective coating applied.
Figure 4B:
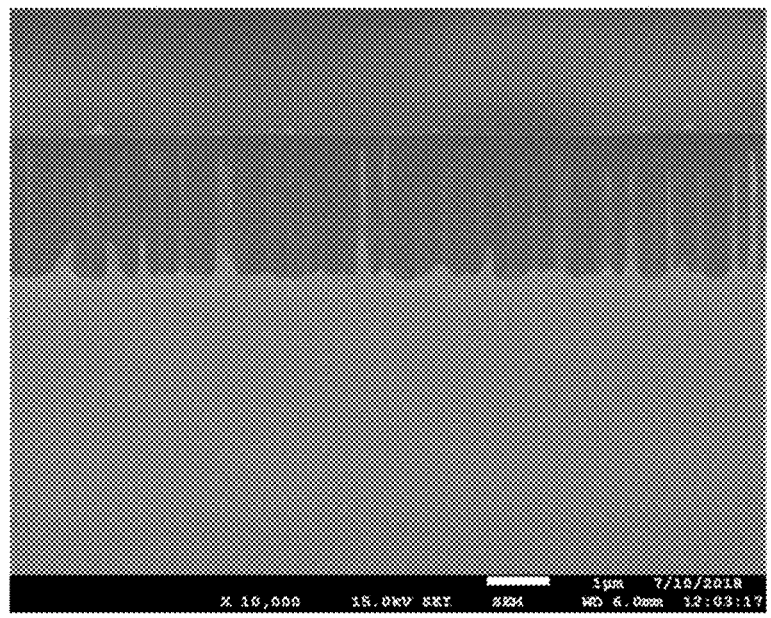
Figure 4C:
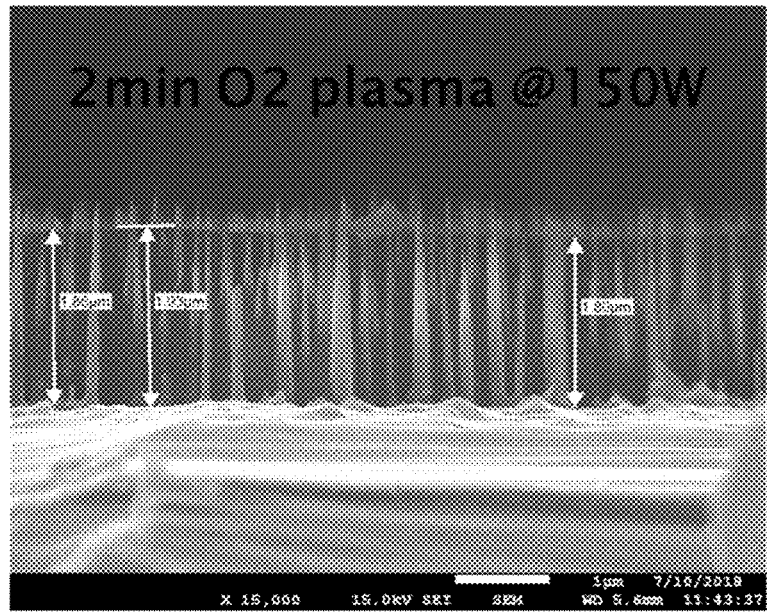
FIGS. 4C-4D show a cross-section of a nanotextured material with a protective coating partially removed by plasma etching (2 min of oxygen plasma at 150 W).
Figure 4D:
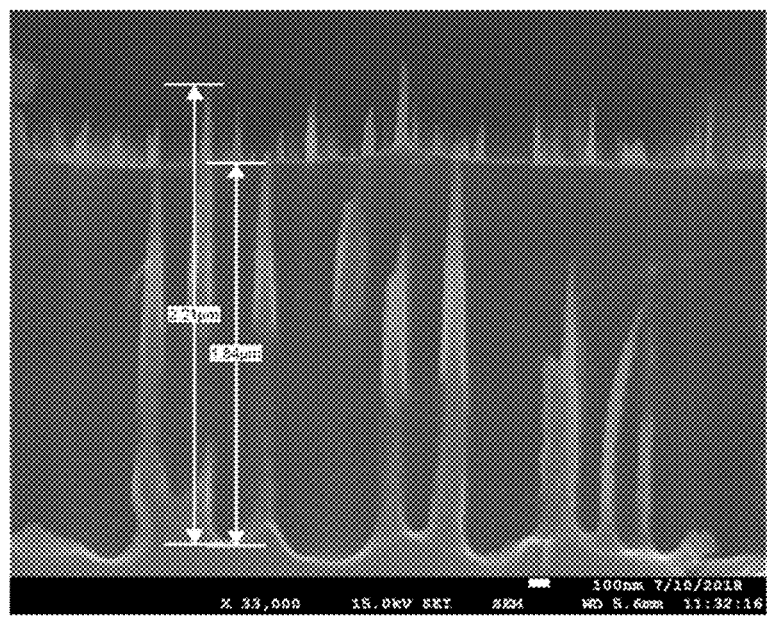

FIGS. 4A-4B show an electron micrograph of a rough silicon surface with an array of pillars fully coated within protective layer (photoresist polymer) before treatment by oxygen plasma. FIGS. 4C-4D are electron micrographs of the rough silicon surface after treatment by oxygen plasma—ca. 300 nm of the top of the pillars are exposed (protectant-free) and prepped for surface modification. As an artifact of sample preparation, the first row of nanopillars appears substantially more exposed and is not representative. In one embodiment, the nanostructures may be modified below the tip, either with the tip modified differently or not at all. For example, nanoimprint lithography could be used to imprint a polymer layer to a certain depth from the tip of the nanostructures. Further, the base of the nanostructure could be modified after the tip of the nanostructure is protected with a hardmask. In one embodiment, metal is bound to the nanostructure tip, such as through the use of a chelator.

Various patterned functionalization methods have been reported like: (i) photochemical methods that use UV, (ii) microcontact printing that uses gold particles and thiols, (iii) microfluidic networks that use high aspect ratio of polydimethylsiloxane ("PDMS") capillary channels, (iv) spotting or spraying (industrial methods), (v) dip-pen lithography, and (vi) atomic force microscopy ("AFM") surface modification. Although successful in localized surface functionalization, most of these methods can only be used on smooth, solid substrates. In contrast with smooth surface modification, embodiments herein provide a mechanism to address layered patterning of novel/reactive chemistries on surfaces that are already rough (an initial level of patterning).

Figure 5:
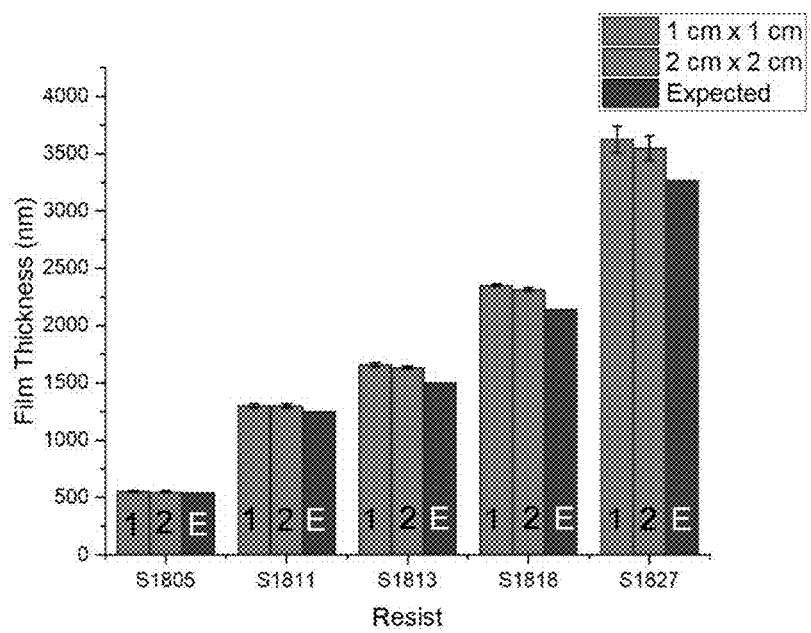
FIG. 5 is a graph of the resist thickness for various polymers deposited on a smooth silicon material.

FIG. 5 shows the thickness of different layers of photoresist, which shows how different thicknesses are available using resists of different viscosity. The expected is calculated for a 4 inch wafer and we are now showing that it can be scaled down to smaller wafers without worry using the same formulas.

Figure 6:
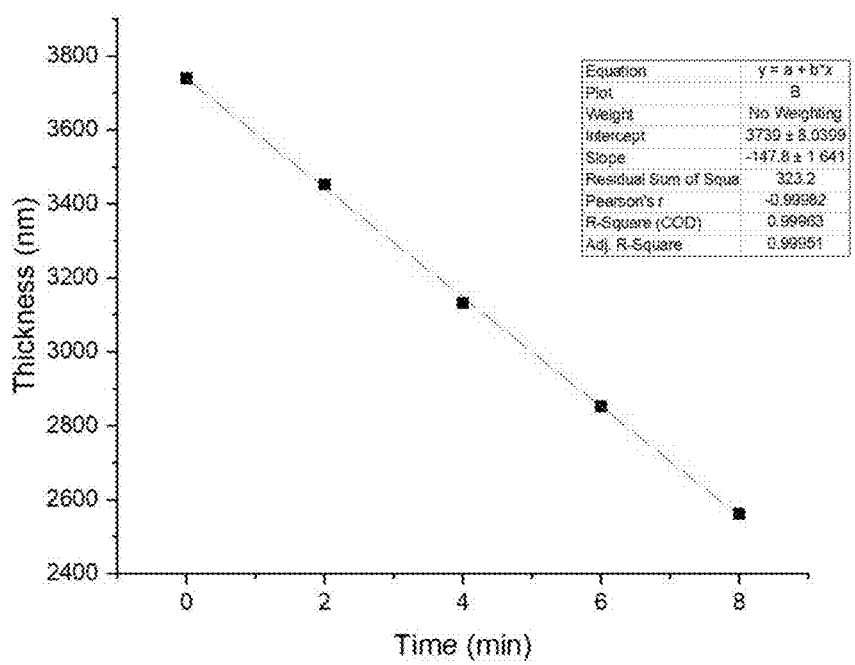
FIG. 6 is a graph of the reduction in thickness over time for one embodiment of removing of the protective coating applied to a nanotextured material. The graph represents an example for smooth silicon surfaces and was used to study etching time on nanotextured materials.
Figure 7:
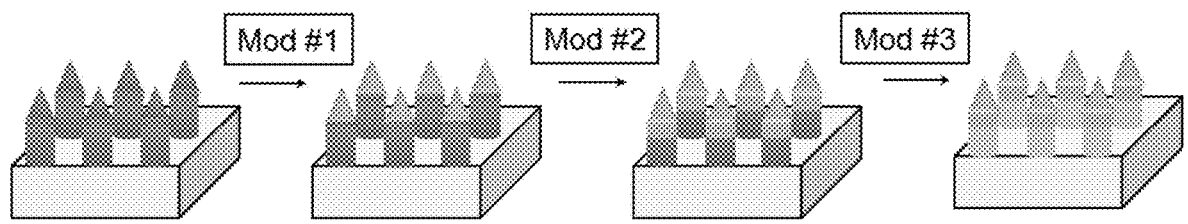
FIG. 7 shows multifunctionalized nanopillars. The illustrated embodiment works as long as chemistries involved in additional layers of modifications do not interfere with those already present. This is possible with, for example, amine-, carboxyl-, and thiol-terminated silanes.
Figure 8:
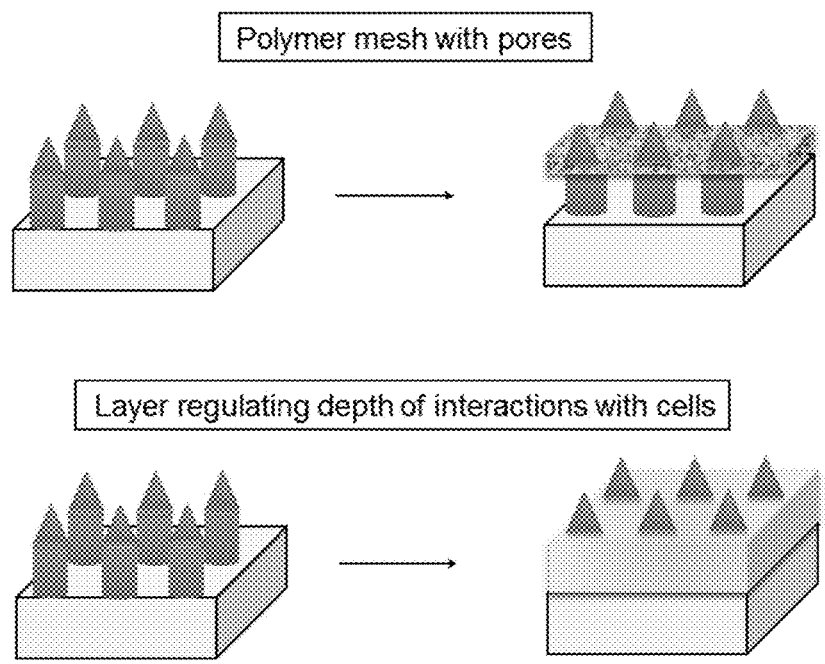
FIG. 8 shows applications of the materials functionalization approach that allows for scavenging of product or drug delivery (top) or the regulation of interactions with cells by placing limits on the length of needles that are allowed to penetrate cells walls and membranes (bottom).
Figure 9A:
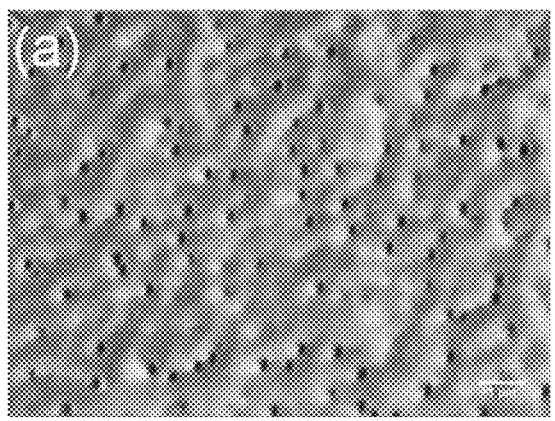
FIGS. 9A-9B show top views using a scanning electron microscope ("SEM") in Gentle Beam mode of a nanotextured substrate, where
Figure 9B:
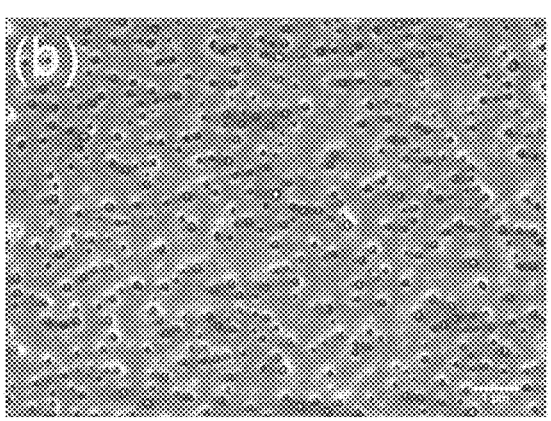
Figure 9C:
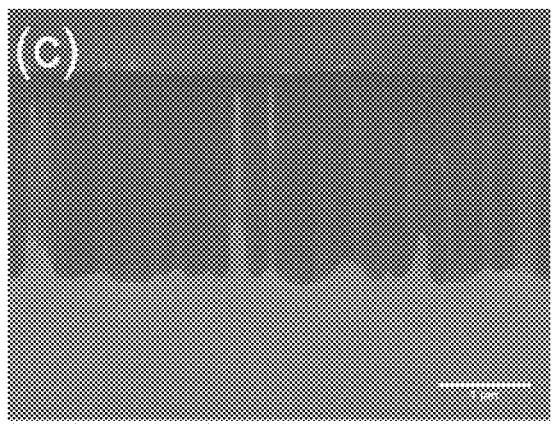
FIGS. 9C-9D show cross sections of the same sample of material, where
Figure 9D:
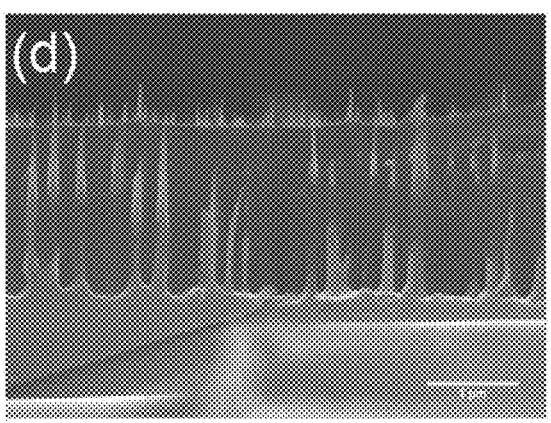
Figure 10A:
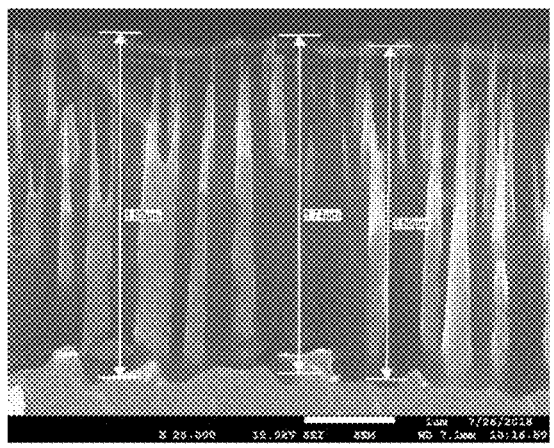
FIGS. 10A-C are SEM images of nanotextured surface with long pillars (~3.6 μm) with protective layer.
Figure 10B:
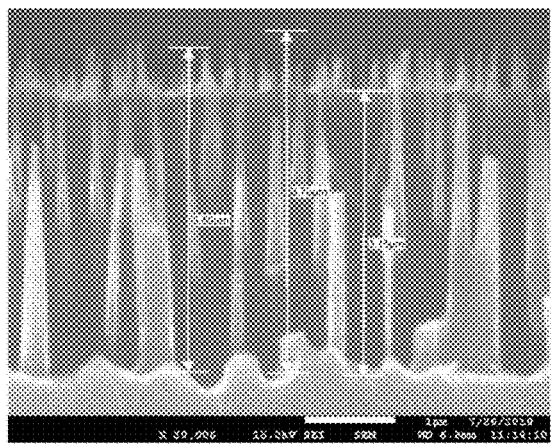
Figure 10C:
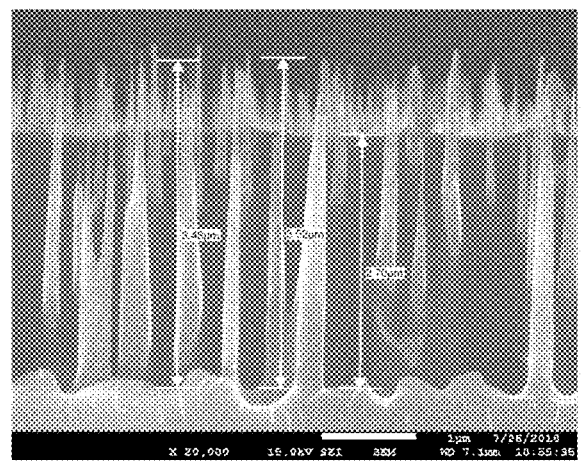
Figure 11A:
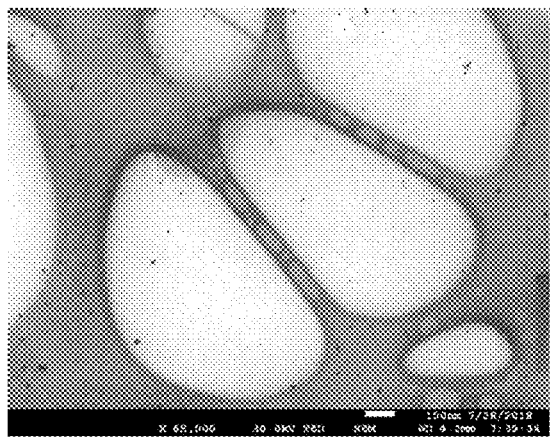
Figure 11B:
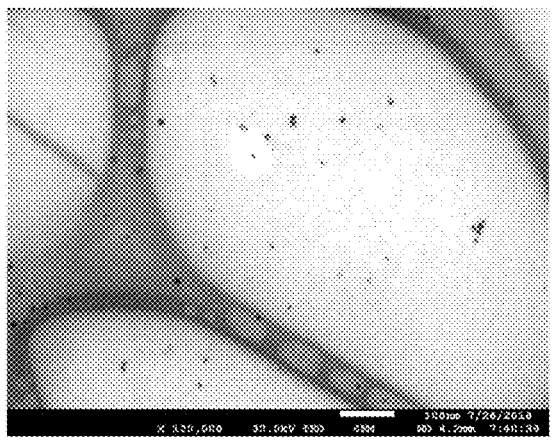
Figure 11C:
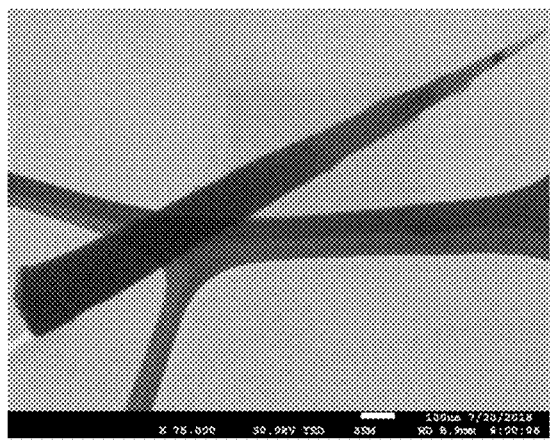
Figure 11D:
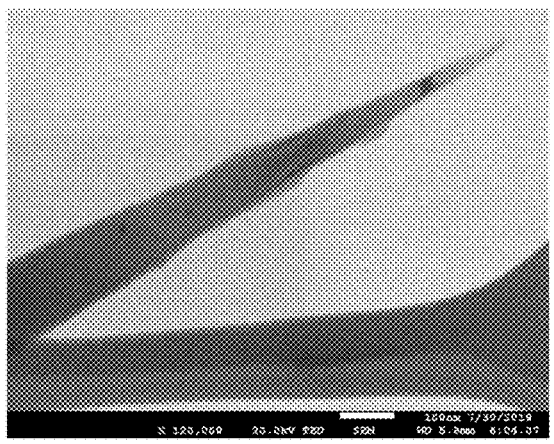

FIG. 6 shows one mechanism for exposing the tips of the structures.

In one embodiment, the nanostructures are functionalized to provide for altered physical properties. For example, increased strength (notably, sheer strength but also compression strength and tensile strength), increased rigidity, and increase hardness. In one embodiment, the nanostructures have a hydrophilic portion, such as the tip, and a hydrophobic portion, such as in the middle, allowing for a flow of aqueous liquids at one height and a flow of nonaqueous liquids at another height, which may provide interaction with different physical structures of the nanostructures as well as different functional groups. As one example, the nanotextured material is able to have a hydrophillic middle layer in between hydrophobic tips and bases and then force aqueous liquids to flow in the middle The reverse may also be true. Another embodiment has an oil layer flowing through mid-pillar height with aqueous above and below for some certain application (e.g., a specific chemical reaction—introducing or removing chemical species as needed or as building up and inhibit, respectively).

Notably, some embodiments may include a nanotextured material that has feature heterogeneity. Nanotextured materials may, for example, have conditions that result in surfaces where occasionally we have a nanoprotrusion of length 30-50% longer than the bulk. The removal of the photoresist to expose the tips of the nanostructures can be controlled to select, for example, for only tips of a certain height, which may not represent the bulk of the nanostructures.

Experimental Results

Experimental studies were undertaken to examiner the functionalized nanostructures. Initially, the nanotextured surface, specifically the protrusions or pillars, were completely covered with PR. Methods were checked to understand how to complete this process on full wafers or smaller pieces of the wafers to save on materials and to allow to additional testing/replication from a single etched wafer.

Generally, the experiments utilized nanoprotrustions with a length and density of ~3.4 µm 4 pillars/µm$^2$, respectively. The wafers were mainly cut into pieces of size 1.5×1.5 cm$^2$. Consideration was given as to whether there is a difference between photoresist thicknesses on smooth silicon substrates cut into 1×1 and 2×2 cm$^2$, and there was none.

Experiments were conducted on photoresists of a variety of viscosities and chemical compositions (e.g., S1805, S1811, S1813, S1818, S1827 from the Shipley MICROPOSIT' series). In the end, the 51818 photoresist was chosen as being most compatible with pillars ~3.5 µm tall (bSi #172 was tested). It routinely gave the best coverage and had a viscosity that allowed for uniform penetration down to the base of the nanoprotrusions.

Following photoresist selection, spin coating conditions were studied by comparison with results on smooth wafers. A first check of S1818 on smooth wafer at speeds: 2000 and 3000 rpm (time: 35 s; acceleration: 1500) indicated that there are differences in film thickness depending on rpm: for 2000~3 µm and for 3000~2.4 µm. The process tested consisted of a one-step process or a two-step process:

1-step process (1s)—3000/1500 (acceleration)/35 s
2-step process (2s)—700/350/5 s and 3000/1500/30 s In of these experiments, baking proceeded 115° C. for 1 min. In the end, it was concluded from SEM images that the one-step process was superior. The one-step process was used for wafer slated for tip exposure and tip functionalization described below.

After coating with the photoresist, tips of the nanoprotrusions where then exposed using reaction ion etching ("ME") using $O_2$ plasma. The conditions for this process were in accordance with known techniques for ME. The etching not only exposes the regions to be modified by removing some of the resist, but also hydroxylates the surface (as indicated by the water contact angle). The RIE conditions were: $O_2$ 24 sccm; Pressure 170 mTorr; and RF power 150 W. The properties of the surfaces changed dramatically right away as silicon tips became exposed. Before plasma etching, water contact angles averaged 78° with complete S1818 PR coverage. After just two minutes of plasma, the contact angle decreased to 12°. Micron-length spikes are exposed with 6 min ME; longer ME exposes majority of spike.

Figure 12A:
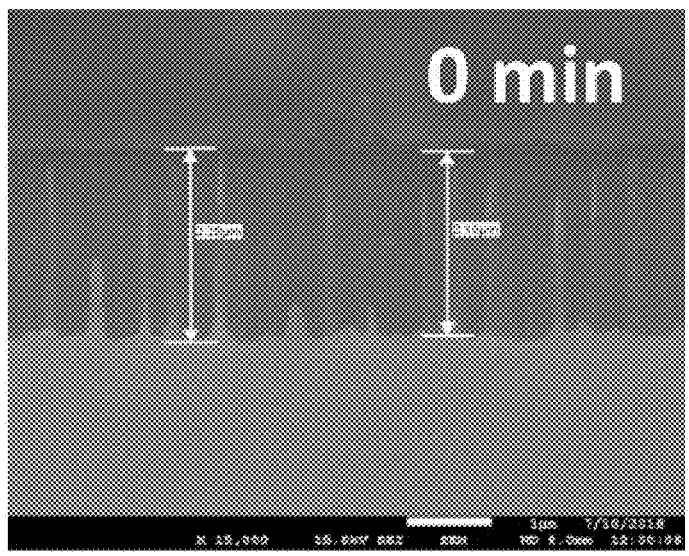
FIGS. 12A-12C show coated nanostructures before (FIG. 12A) and after 2 min of oxygen plasma exposure (FIGS. 12B-12C).
Figure 12B:
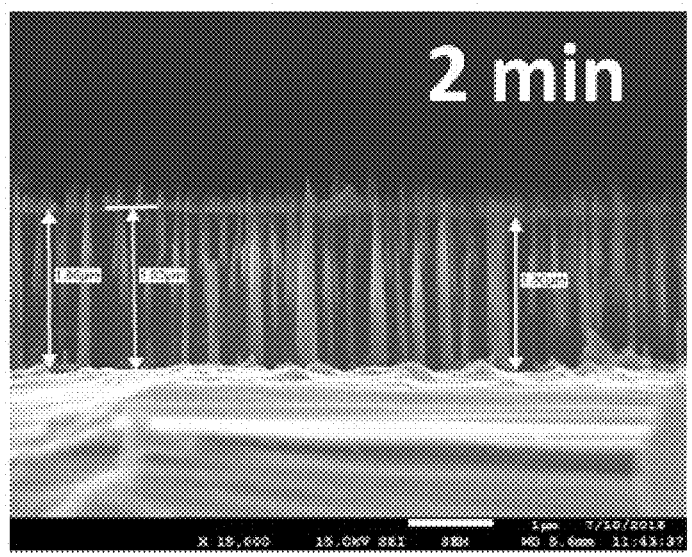
Figure 12C:
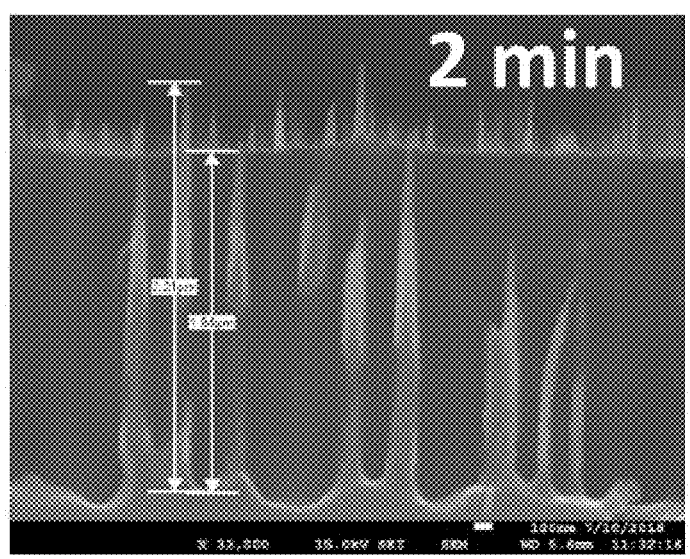

To modulate the proportion of the tip that was exposed, time was varied, with experiments examining 2, 3, 6 and 8 minute cycles and compared them to non-exposed controls (0 mins in FIG. 12). Tip exposure was characterized using Scanning Electron Microscopy. Gentle-beam and regular-mode image techniques were used to understand the state of the surfaces following oxygen plasma etching. The assorted of views (top and tilts of 90°, 18°, 45°) demonstrate the successful exposure of the top segments of the nanoprotrusions.

At this stage, the coated wafer could be cut, such as by a diamond knife to produce smaller samples for testing and further modification.

Next, the surfaces of the exposed tips were chemically modified using silanization by MPMDMS to prepare for subsequent binding of gold nanoparticles. Here, the tip-exposed wafers were covered in a solution of 1% v/v MPMDMS solution. The reaction was allowed to proceed for 1-2 hours at room temperature. Excess silanes were then removed by washing/cleaning of the wafers with toluene. Silanization was completed by further annealing for 15 min at 120° C.

Notably, there were many problems observed for known solvents or silanes potentially removing additional resist and exposing larger segments of the nanoprotrusions and/or making surface modification of the tips inefficient/impractical. It was found that the S1818 photoresist was soluble/removed by the following solvents: methanol, ethanol, isopropyl alcohol, methylene chloride, and acetone but not soluble in $H_2O$/toluene solutions. Further, silanes (especially mercapto- and amino-based variants, etc.) interact with PR 51818.

Photoresist removal or layer modification during silanization was monitoring by recording of the spectrum of the reacting solutions. The photoresist was colored and has a characteristic spectrum in acetone, for example, and the silanes are UV-active in water. The silicon wafers with S1818 resist on them were immersed in 1.5 mls of 2.5% silane solution and sonicated for 15 seconds. There were no indicates that resist was removed during silane process.

Once the surfaces of the exposed tips were modified, the chemically heterogeneous nature of the surfaces of the nanoprotrusions was examined by immobilization of gold nanoparticles to the surface. For one set of tests, after annealing, all remaining photoresist was washed with acetone (no sonication). Following removal, a solution of Au-nanoparticles was added and the suspension was rocked for 48 hours. If successful, the gold nanoparticles should only be localized to the tips. Further, a positive control test was used where photoresist was removed after binding of the gold nanoparticles. An alternative method (or a positive control) would be to immobilize the Au nanoparticles to the surface and then remove the photoresist. Both were achieved in these experiments.

With positive controls, wafers with chemically-modified tips were exposed to nanoparticles prior to remove of photoresist. After silane annealing steps, a solution of Au-nanoparticles was added directed to wafers with a photoresist layer remaining. This suspension was also rocked for 48 hours. Following binding of the gold nanoparticles, S1818 photo-resist was washed away with 3× treatment of acetone (FIGS. 13A-13B). Notably, in many cases it was harder to remove photoresist after silanization (FIG. 14).

In both cases of the photoresist being removed before and after the nanoparticle modification, Au— nanoparticles were suspended in water. Here, 1.5-2 ml of suspension were added per well of 6-well plates with wafers inside. The plates were rocked for 48 hours. Wafers were washed thoroughly with water following the Au— nanoparticle treatment.

As used herein, the singular forms "a," "an," and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the stated value. For example, about 0.5 would include 0.45 and 0.55, about 10 would include 9 to 11, about 1000 would include 900 to 1100.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

We claim:

1. A method for functionalizing a nanotextured material comprising:
   forming a nanotextured material having a plurality of structures extending in a first dimension and each of the plurality of structures having a distal portion;
   applying a resist coating on the nanotextured material, the resist coating leaving an uncoated distal portion of the plurality of structures corresponding to at least some of the distal portions of the plurality of structures;
   modifying the uncoated distal portions with a first functional group; and
   removing the resist coating.

2. The method of claim 1, wherein applying the resist coating comprises applying the resist coating comprises spin coating the nanotextured material.

3. The method of claim 2, wherein the resist coating fills space between each of the plurality of structures.

4. The method of claim 2, wherein the exposed distal portions are functionalized with the first function group and remaining portions of the plurality of structures are not functionalized with the first functional group.

5. The method of claim 1, wherein applying the resist coating further comprises removing a portion of the resist coating to expose the exposed distal portions.

6. The method of claim 1, further comprising:
   prior to applying the resist coating, the nanotextured material is washed with tolulene; and modifying the exposed distal portions comprises silanization, wherein the silanization comprises application of a silane solution having 0.001% to 1% v/v silane in a toluene solvent.

7. The method of claim 1, further comprising positioning a polymeric network on the nanostructures.

8. The method of claim 1, wherein a mask is applied to the exposed distal portions forming masked distal portions and further comprising application of a second etching after removal of the resist coating, the second etching removing proximate portions of the nanostructures that are not the masked distal portions.

9. A method for functionalizing a nanotextured material comprising:
   forming a nanotextured material having a plurality of structures extending in a first dimension and each of the plurality of structures having a distal portion;
   forming a resist coating on the nanotextured material by applying the resist coating to the nanotextured material and removing a portion of the resist coating, exposing distal portions;
   modifying the exposed distal portions by silanization; and
   removing the resist coating.

10. The method of claim 9, wherein the exposed distal portions are functionalized with the first function group and remaining portions of the plurality of structures are not functionalized with the first functional group.

11. The method of claim 9, wherein the plurality of structures are heterogeneous.

12. The method of claim 9, wherein the silanization comprises application of a silane solution having 0.001% to 1% v/v silane in a first organic solvent.

13. The method of claim 12, wherein, prior to applying the resist coating, the nanotextured material is washed with the first organic solvent, the first organic solvent comprising toluene.

14. The method of claim 13, wherein the silane is a chlorosilane.

15. A method for functionalizing a nanotextured material comprising:
   forming a nanotextured material having a plurality of structures extending in a first dimension and each of the plurality of structures having a distal portion;
   applying a resist coating on the nanotextured material, wherein at least some of the distal portions of the plurality of structures are exposed beyond the resist coating;
   modifying the exposed distal portions with a first functional group;
   removing the resist coating; and
   applying a mask to the exposed distal portions forming masked distal portions and further comprising application of a second etching after removal of the resist coating, the second etching removing proximate portions of the nanostructures that are not the masked distal portions.

16. The method of claim 15, wherein the resist coating fills space between each of the plurality of structures.

17. The method of claim 15, modifying the exposed distal portions comprises silanization.

18. The method of claim 17, wherein the silanization comprises application of a silane solution having 0.001% to 1% v/v silane in a first organic solvent.

19. The method of claim 15, wherein the exposed distal portions are functionalized with the first function group and remaining portions of the plurality of structures are not functionalized with the first functional.

20. The method of claim 15, wherein, prior to applying the resist coating, the nanotextured material is washed with the first organic solvent, the first organic solvent comprising toluene.

* * * * *